(12) United States Patent
Haitsuka et al.

(10) Patent No.: US 10,307,540 B2
(45) Date of Patent: *Jun. 4, 2019

(54) NEEDLELESS SYRINGE

(71) Applicant: DAICEL CORPORATION, Osaka (JP)

(72) Inventors: Masahiro Haitsuka, Hyogo (JP); Masayuki Ueda, Tokyo (JP)

(73) Assignee: Daicel Corporation, Osaka (JP)

( * ) Notice: Subject to any disclaimer, the term of this patent is extended or adjusted under 35 U.S.C. 154(b) by 197 days.

This patent is subject to a terminal disclaimer.

(21) Appl. No.: 15/273,554

(22) Filed: Sep. 22, 2016

(65) Prior Publication Data

US 2017/0007768 A1     Jan. 12, 2017

Related U.S. Application Data

(63) Continuation of application No. 13/983,536, filed as application No. PCT/JP2012/052488 on Feb. 3, 2012, now Pat. No. 9,474,860.

(30) Foreign Application Priority Data

Feb. 4, 2011    (JP) ................................ 2011-023315

(51) Int. Cl.
    *A61M 5/30*        (2006.01)
    *A61M 5/20*        (2006.01)
    *A61M 5/28*        (2006.01)

(52) U.S. Cl.
    CPC ............ *A61M 5/30* (2013.01); *A61M 5/2046* (2013.01); *A61M 5/288* (2013.01); *A61M 2005/2013* (2013.01); *A61M 2205/42* (2013.01)

(58) Field of Classification Search
    CPC ...... A61M 5/30; A61M 5/288; A61M 5/2046; A61M 2005/2013
    See application file for complete search history.

(56) References Cited

U.S. PATENT DOCUMENTS

| | | |
|---|---|---|
| 2,667,874 A | 2/1954 | Dickinson et al. |
| 3,115,133 A | 12/1963 | Morando |

(Continued)

FOREIGN PATENT DOCUMENTS

| | | |
|---|---|---|
| JP | 11-276584 | 12/1999 |
| JP | 2006522614 | 10/2006 |
| WO | WO 01-91835 A1 | 12/2001 |

OTHER PUBLICATIONS

International Search Report, PCT/JP2012/052488, dated May 15, 2012.

(Continued)

*Primary Examiner* — Bradley J Osinski
(74) *Attorney, Agent, or Firm* — Knobbe Martens Olson & Bear LLP

(57) ABSTRACT

The present application relates to a needleless syringe for injecting an injection objective substance into an injection target area without using an injection needle. In one aspect, the needleless syringe includes a main syringe body containing the injection objective substance with the use of a sealing member, a pressurizing unit provided in the main syringe body and configured to pressurize the injection objective substance, a flow passage unit defining a flow passage of the pressurized injection objective substance to be discharged to the injection target area and a preparatory filling unit configured to fill the flow passage unit with a part of the injection objective substance by destroying a part of the sealing member before the injection objective substance is pressurized. According to some embodiments, it is pos- (Continued)

sible to mitigate the load exerted on the nozzle during the injection and reduce the noise without deteriorating a syringe user convenience.

15 Claims, 11 Drawing Sheets

(56) References Cited

U.S. PATENT DOCUMENTS

| | | |
|---|---|---|
| 6,645,170 B2 | 11/2003 | Landau |
| 6,673,035 B1 | 1/2004 | Rice et al. |
| 6,979,310 B2 | 12/2005 | Navelier et al. |
| 7,156,822 B2 | 1/2007 | Navelier et al. |
| 7,513,885 B2 | 4/2009 | Navelier et al. |
| 9,474,860 B2 * | 10/2016 | Haitsuka ................ A61M 5/30 |
| 2003/0097093 A1 | 5/2003 | Navelier et al. |
| 2004/0215136 A1 | 10/2004 | Navelier et al. |
| 2004/0215137 A1 | 10/2004 | Navelier et al. |
| 2006/0189927 A1 | 8/2006 | Alexandre et al. |
| 2010/0179473 A1 | 7/2010 | Genosar |

OTHER PUBLICATIONS

Extended European Search Report received in International Application No. PCT/JP2012/052488 dated Jun. 16, 2014.
European Office Action, dated Jun. 22, 2016, received in corresponding European Patent Application No. 12741688.1.

* cited by examiner

NEEDLELESS SYRINGE

RELATED APPLICATIONS

This Application is a continuation of and claims benefit from U.S. application Ser. No. 13/983,536, filed on Nov. 22, 2013, which is a U.S. National Stage filing under 35 U.S.C. § 371 of International Application No. PCT/JP2012/052488 filed on Feb. 3, 2012, each of which is incorporated herein by reference in its entirety. The PCT application also claimed priority to and the benefit of Japanese Patent Application No. 2011-023315 filed on Feb. 4, 2011 in the Japan Patent Office, which is incorporated herein by reference.

TECHNICAL FIELD

The present invention relates to a needleless syringe (needle-free syringe or needleless injector) with which an injection objective substance is injected into an injection target area of a living body without using any injection needle.

BACKGROUND ART

In relation to a needleless syringe with which the injection is performed without using any injection needle, a construction is adopted in some cases such that an injection component is injected or discharged by applying a pressure to an accommodating chamber in which an injection solution is accommodated, by means of a pressurized gas or a spring. For example, in the case of a needleless syringe disclosed in Patent Document 1, an injection solution, which is enclosed by an upstream side piston plug and a downstream side piston plug, is pressurized and allowed to flow into the nozzle, and thus the injection solution is discharged from the discharge port (injection port) thereof. In this situation, the pressurized injection solution is allowed to flow all at once into the nozzle which is in the atmospheric pressure state. Therefore, the pressure, which is received by the main nozzle body from the injection solution, is extremely changed. For this reason, for example, it is feared that the nozzle may be deformed and/or destroyed, and any noise may be generated during the injection.

On the other hand, for example, in the Patent Document 2, such an arrangement is disclosed that the interior of the nozzle is made filled with a part of an injection solution before injecting the injection solution by using a needleless syringe. Specifically, as shown in FIG. 2 of Patent Document 2, such a state is given before the use of a syringe that the accommodated injection solution is prohibited from flowing to the side of the nozzle by means of a ball valve which functions as a sealing member for an accommodating chamber for the injection solution. When the syringe is used, a grip of a main syringe body is twisted or screwed, and thus the ball valve is relatively moved in the main syringe body. A communicated state is given between the accommodating chamber and the nozzle by means of a groove arranged in the vicinity of the ball valve (see FIG. 4 of Patent Document 2), and the nozzle is made filled with the injection solution.

PRECEDING TECHNICAL DOCUMENTS

Patent Documents

Patent Document 1: JP2006-522614A;
Patent Document 2: U.S. Pat. No. 6,645,170.

SUMMARY OF THE INVENTION

Task to be Solved by the Invention

When the pressure is applied to the injection solution as the driving force for injecting the injection solution in the needleless syringe, it is feared that the excessive load and the shock exerted on the nozzle as well as the generation of the noise may arise due to the inflow of the injection solution into the interior of the nozzle all at once, if the interior of the nozzle is in the atmospheric pressure state as described above. On the other hand, in the case of the needleless syringe having such a structure that the interior of the nozzle is made filled with the injection solution before the injection or discharge of the injection solution by moving the ball valve in the main syringe body as in the conventional technique, such a state is given upon the actual injection that the ball valve substantially remains in the flow passage between the accommodating chamber and the nozzle. Therefore, the ball valve may act as the resistance against the flow of the injection solution during the injection. As a result, the energy of the pressurized injection solution is dispersed by the ball valve, which is the factor to inhibit the efficient injection. In order to dissolve this inconvenience, it is necessary to perform, for example, the scale up of the pressurizing unit, and the convenience of the syringe is deteriorated.

Taking the foregoing problem into consideration, an object of the present invention is to provide a needleless syringe which makes it possible to mitigate the load exerted on the nozzle during the injection and reduce the noise without deteriorating the convenience of a user when the needleless syringe is used.

Solution for the Task

In order to solve the problem as described above, the present invention adopts the following construction. That is, a sealing member, which defines a part of an accommodating unit for accommodating an injection objective substance including an injection solution, is formed destroyably, and a part of the sealing member is destroyed so that a flow passage unit, into which the injection objective substance is allowed to flow, is thereby made filled with a part of the injection objective substance before the injection of the injection objective substance. That is, in the present invention, the sealing member is formed destroyably, and thus both of the mitigation of the load exerted on the flow passage unit during the injection and the mitigation of the resistance force exerted on the injection objective substance during the injection are fulfilled.

Specifically, the present invention resides in a needleless syringe for injecting an injection objective substance into an injection target area of a living body without using any injection needle; the needleless syringe comprising a main syringe body; an accommodating unit which accommodates the injection objective substance by the aid of a sealing member in an accommodating chamber provided in the main syringe body; a pressurizing unit which pressurizes the injection objective substance accommodated in the accommodating unit to move or destroy the sealing member thereby so that the injection objective substance is discharged to outside; a flow passage unit which forms a discharge port with respect to the injection target area and which defines a flow passage so that the injection objective substance pressurized by the pressurizing unit is discharged via the discharge port to the injection target area; and a preparatory filling unit which fills the flow passage unit with a part of the injection objective substance accommodated in the accommodating chamber by destroying a part of the sealing member before pressurization is performed by the pressurizing unit.

In the needleless syringe according to the present invention, the pressure is applied to the injection objective substance, and thus the movement of the injection objective substance is facilitated. As a result, the injection objective substance flows into the flow passage of the flow passage unit, and the injection objective substance is injected or discharged from the discharge port (injection port) to the injection target area. The injection objective substance contains the component for which the efficacy is expected at the inside of the injection target area. The pressure, which is applied from the pressurizing unit as described above, is the driving source upon the injection or discharge thereof. Therefore, any accommodating state of the injection objective substance in the needleless syringe is available without causing any problem, and any specified physical form of the injection objective substance is available without causing any problem, including, for example, liquid, fluid, for example, in a gel form, powder, solid, for example, in a granular form, provided that the injection objective substance can be injected or discharged by the pressurizing unit.

For example, the injection objective substance is a liquid. Even when the injection objective substance is a solid, it is also allowable to use a solid in a gel form, provided that the fluidity, which makes it possible to discharge the injection objective substance, is secured or guaranteed. Further, the component, which is to be fed into the injection target area of the living body, is contained in the injection objective substance. The component may exist in such a state that the component is dissolved in the injection objective substance, or the component may be in such a state that the component is simply mixed without being dissolved. For example, the component to be fed includes, for example, vaccine for enhancing antibody, protein for beauty, and cultured cells for regenerating hair. The injection objective substance is formed by containing the component in a liquid or a fluid in a gel form or the like so that the component as described above can be discharged.

Further, as for the pressurizing source for the injection objective substance, it is possible to utilize various pressurizing sources provided that the injection objective substance can be discharged by being pressurized. The pressurizing source is exemplified, for example, by those which utilize the elastic force brought about by a spring or the like, those which utilize the pressurized gas, those which utilize the combustion of a propellant or pyrotechnic charge, and those which utilize an electric actuator (for example, motor, piezoelectric element or the like) for performing pressurization.

In this context, the injection objective substance is accommodated in the accommodating chamber by the accommodating unit before being pressurized by the pressurizing unit. The sealing member forms a part of the accommodating unit. The sealing member is formed by a member which is destroyable by means of any external factor. That is, the sealing member has, for example, a strength to such an extent that the accommodating state can be appropriately maintained in view of the fact that the injection objective substance is accommodated. However, a part of all of the sealing member may be destroyed by any external factor including, for example, the application of any external force. In the case of the needleless syringe according to the present invention, the injection objective substance is accommodated by the accommodating unit by the aid of the sealing member as described above.

Further, the preparatory filling unit destroys the part of the sealing member before being pressurized by the pressurizing unit, and thus the part of the injection objective substance contained in the accommodating chamber is allowed to leak out. The part of the injection objective substance is introduced into the flow passage unit, and thus the flow passage unit is previously or preparatorily filled with the injection objective substance. In this context, the phrase "part is destroyed" refers to the destroyed state which is such a state that the injection objective substance accommodated in the accommodating chamber may leak out to the outside of the chamber, but the destroyed state is at a low level as compared with a destroyed state in which the injection objective substance may be discharged from the accommodating chamber to such an extent that a large amount of the injection objective substance is injected or discharged from the discharge port of the syringe to the injection target area as injected or discharged during the main injection operation. Accordingly, when the pressurization is executed by the pressurizing unit, then the pressurized injection objective substance flows into the flow passage unit having been filled with the injection objective substance, and the injection or discharge is performed. As a result, it is possible to suppress the application of the sudden pressure and the shock to the flow passage unit during the discharge, and it is possible to mitigate the noise which would be otherwise caused by the sudden fluctuation of the pressure.

Further, the sealing member is formed by the member which is destroyable by the external factor. Therefore, when the pressurization is executed by the pressurizing unit, the sealing member may become to be in such a state that the sealing member is more destroyed as compared with the state of being destroyed by the preparatory filling unit. Therefore, it is possible to relieve or alleviate the resistance force exerted on the injection objective substance by the sealing member during the injection. In this situation, the sealing member may be moved from the position provided before the injection. Alternatively, it is also allowable that the sealing member is not moved from the position provided before the injection. In any case, owing to the fact that the sealing member is the destroyable member, the resistance force, which is exerted on the injection objective substance by the sealing member during the injection, is relieved or alleviated.

In this context, the needleless syringe as described above may be constructed such that the accommodating unit is formed by providing the sealing member on one end side of the accommodating chamber and providing a second sealing member on the other end side of the accommodating chamber so that the accommodating chamber is hermetically closed. Further, in this arrangement, the flow passage unit may be filled with the part of the injection objective substance by means of a load exerted on the injection objective substance by the second sealing member when the part of the sealing member is destroyed by the preparatory filling unit. That is, the second sealing member, which is disposed on the other end side, defines the part of the accommodating chamber, and the second sealing member provides the driving force to introduce or guide the injection objective substance accommodated in the accommodating chamber into the flow passage unit when the part of the sealing member disposed on one end side is destroyed by the preparatory filling unit. The flow passage for the injection, which is formed in the flow passage unit, is generally set such that the flow passage diameter is extremely small in many cases as compared with the size of the accommodating chamber, in order to apply a predetermined penetrating force to the injection objective substance as well. Therefore, when the second sealing member is used as the source of the driving force for the introduction into the flow passage unit as described above, it is possible to reliably achieve the previous or preparatory filling in the flow passage unit without excessively enlarging the size of the needleless syringe itself.

In this context, the second sealing member may be constructed such that the second sealing member applies a predetermined pressure to the injection objective substance by deforming a part of the second sealing member when the accommodating unit and the pressurizing unit are combined at an assembly time of the needleless syringe. That is, the second sealing member is deformed during the assembling, and the restoring force, which is accumulated therein, is utilized as the driving force to preparatorily introduce the injection objective substance into the flow passage unit. Therefore, the easiness of deformation, which is to such an extent that the assembling is not prohibited, is required for the second sealing member. On the other hand, for example, it is preferable that the elastic force and the shape of the member are set to be appropriate so that the sufficient driving force, i.e., the applied state of the predetermined pressure as described above is secured. It is preferable that the predetermined pressure has a magnitude of such an extent that the destruction is not performed by the preparatory filling unit and the sealing member is not destroyed by only the predetermined pressure, in order to secure the appropriate accommodation of the injection objective substance in the accommodating unit.

In this context, the needleless syringe as described above may be constructed such that the sealing member is destroyed or moved in an axial direction by applying a pressure in the axial direction of the main syringe body to the injection objective substance accommodated in the accommodating unit by the pressurizing unit. Further, in this arrangement, the preparatory filling unit has a movable destroying member which is movable toward the sealing member to destroy the part of the sealing member before performing the pressurization by the pressurizing unit; and the movable destroying member is in a non-contact state with respect to the sealing member when the movable destroying member is disposed at a first position, while the movable destroying member is brought in contact with the sealing member to destroy the part of the sealing member when the movable destroying member is moved from the first position to a second position.

In the construction described above, the movable destroying member, which is possessed by the preparatory filling unit, is provided so that the movable destroying member is relatively movable with respect to the sealing member in the predetermined direction irrelevant to the direction of pressurization exerted on the injection objective substance by the pressurizing unit. When the needleless syringe is not used (unused), the movable destroying member is placed at the first position. The movable destroying member is moved to the second position before the use, and thus the movable destroying member is brought in contact with the sealing member to destroy the part thereof. The pressurization is executed by the pressurizing unit in this state. Accordingly, the sealing member is further destroyed, and the discharge of the major part of the injection objective substance is executed. Therefore, it is enough for the user of the needleless syringe to perform the movement of the movable destroying member from the first position to the second position as the preparatory stage to perform the injection. Accordingly, it is possible to execute the injection without deteriorating the convenience of the needleless syringe.

The needleless syringe described above may be constructed such that the movable destroying member is provided on a side of the flow passage unit, and a part of the movable destroying member is in a state of protruding in a side on which the discharge port of the flow passage unit is open when the movable destroying member is disposed at the first position; and the movable destroying member, which has protruded, is moved to the second position to destroy the part of the sealing member when the movable destroying member is pressed in a state in which the discharge port is brought in contact with the injection target area of the living body. That is, in this construction, the movement of the movable destroying member from the first position to the second position is realized by bringing the discharge port formed in the flow passage unit into contact with the injection target area, and pressing the part of the protruding movable destroying member. According to this construction, the user of the needleless syringe can realize the preparatory filling or charging into the flow passage unit by performing the same operation as that performed for the mode of use of the conventional needleless syringe, i.e., by bringing the needleless syringe into contact with the injection target area. Therefore, it is possible to avoid the deterioration of the convenience thereof.

In the case of the construction described above, an end portion of the movable destroying member disposed at the second position may be constructed to be in a substantially flush state with respect to an outer surface of the flow passage unit for which the discharge port is formed. According to this construction, during the injection, the user scarcely receives the repulsive force etc. from the movable destroying member which protruded. Therefore, it is possible to mitigate the sense of discomfort when the syringe is used.

In this context, in the needleless syringe as described above, it is also preferable to adopt such a construction that the flow passage unit is attached to the main syringe body in such a state that the flow passage unit is relatively movable so that the flow passage unit closely approaches the main syringe body before the pressurization is performed by the pressurizing unit. In this arrangement, the preparatory filling unit is provided on a side of the flow passage unit; and the part of the sealing member is destroyed by the preparatory filling unit, the flow passage unit is filled with the part of the injection objective substance accommodated in the accommodating chamber, and thus the pressurization by the pressurizing unit is made ready to perform, when the flow passage unit closely approaches the main syringe body before the pressurization is performed by the pressurizing unit. That is, in this construction, the flow passage unit and the main syringe body are relatively movable, and the preparatory filling unit is installed on the side of the flow passage unit. Therefore, the preparatory filling unit itself is also relatively movable so that the preparatory filling unit closely approaches the main syringe body although the preparatory filling unit is relatively movable together with the flow passage unit. Even in the case of the construction as described above, the part of the sealing member can be destroyed, and thus the flow passage unit can be preparatorily filled smoothly.

In particular, the needleless syringe described above may be constructed such that the flow passage unit relatively closely approaches the main syringe body by being pressed from a side of the main syringe body in a state in which the discharge port is brought in contact with the injection target area of the living body. According to the construction as described above, the user can realize the preparatory filling or charging into the flow passage unit by performing the same operation as that performed for the mode of use of the conventional needleless syringe, i.e., by bringing the needleless syringe into contact with the injection target area. Therefore, it is possible to avoid the deterioration of the convenience thereof.

In this context, in the needleless syringe as described above, it is also preferable that the sealing member is formed to have a thin film-shaped form, the preparatory filling unit cleaves the thin film, and thus the flow passage unit is filled with the part of the injection objective substance. When the pressurization is performed by the pressurizing unit, the following procedure may be also available. That is, the thin film, which has been already cleaved, is further cleaved to a greater extent, or a portion of the thin film, which is not cleaved, is newly cleaved, and thus the injection objective substance, which remains in the accommodating chamber, may be discharged to the outside of the chamber.

Further, the needleless syringe as described above may adopt the following construction. That is, the preparatory filling unit has a shutoff wall which forms a substantially gas-tight closed space including the discharge port and the injection target area in a state in which the discharge port is brought in contact with the injection target area of the living body, and interior of the closed space brought about by the shutoff wall is made in a negative pressure state in a state in which the part of the sealing member is destroyed, and thus the flow passage unit is filled with the part of the injection objective substance accommodated in the accommodating chamber. According to this construction, the closed space is in the negative pressure state, and thus it is possible to more smoothly realize the situation in which the flow passage unit is preparatorily filled by means of the preparatory filling unit. As described above, the flow passage diameter in the flow passage unit is formed to be relatively small. However, the negative pressure state is formed by the shutoff wall, and thus the inflow of the injection objective substance into the flow passage unit is accelerated. Further, the closed space is formed in the vicinity of the discharge port including the discharge port by means of the shutoff wall. Therefore, it is also possible to suppress the injection objective substance from being widely scattered when the interior of the flow passage unit is filled with the injection objective substance by means of the preparatory filling unit and/or when the injection objective substance is discharged.

The following construction is exemplified as an example of the shutoff wall. That is, the shutoff wall is composed of an elastic member, and the negative pressure state is formed in the closed space in accordance with elastic deformation of the elastic member. Any other material may be adopted provided that the structure is given such that the closed space is formed in the vicinity of the discharge port including the discharge port, and the closed space can be formed in the negative pressure state.

Effect of the Invention

It is possible to provide the needleless syringe which makes it possible to mitigate the load exerted on the nozzle during the injection and reduce the noise without deteriorating the convenience of a user in relation to the needleless syringe.

MODE FOR CARRYING OUT THE INVENTION

A needleless syringe 1 (hereinafter simply referred to as "syringe 1") according to an embodiment of the present invention will be explained below with reference to the drawings. The construction of the following embodiment is described by way of example. The present invention is not limited to the construction of the embodiment.

Figure 4A:
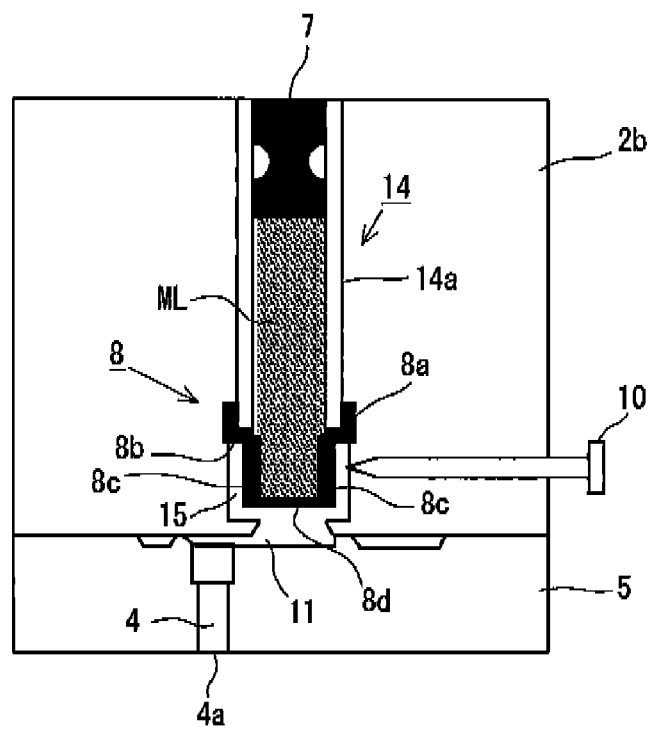
FIG. 4A shows an internal state of the needleless syringe before the interior of the nozzle is preparatorily filled with an injection solution in a first embodiment of the needleless syringe according to the present invention.

In this embodiment, FIG. 1(a) shows a sectional view illustrating the syringe 1, FIG. 1(b) shows a side view illustrating the syringe 1 as viewed from a side of an initiator 20, and FIG. 1(c) shows a side view illustrating the syringe 1 as viewed from a side of nozzles 4 for injecting or discharging an injection solution. In the following description of this application, the injection objective substance, which is injected into the injection target by the syringe 1, is generally referred to as "injection solution". However, this description includes no intention to limit the contents and the form of the substance to be injected. The component, which is to be delivered to the skin structure, may be either dissolved or not dissolved in the injection objective substance. Any specified form of the injection objective substance is available without any problem as well, for which various forms can be adopted, including, for example, liquid and gel form, provided that the injection objective substance can be injected or discharged to the skin structure from the nozzle 4 by performing the pressurization. In this embodiment, the syringe 1 has a main syringe body 2. An accommodating chamber 14, which extends in the axial direction and which has a constant diameter in the axial direction, is provided at a central portion of the main syringe body 2. As shown in FIG. 4A, for example, the accommodating chamber 14 is formed by a cylindrical accommodating chamber wall 14a having a constant thickness. One end of the accommodating chamber 14 is communicated with the combustion chamber 9 which has a diameter that is larger than the diameter of the accommodating chamber 14, via a piston chamber 13 for accommodating a piston 6 as described later on. The remaining other end arrives at the side of a nozzle holder 5 in which the nozzles 4 are formed. Further, the initiator 20 is installed on the side opposite to the communicated portion of the combustion chamber 9 communicated with the accommodating chamber 14 so that the ignition unit thereof is opposed to the communicated portion.

Figure 1:
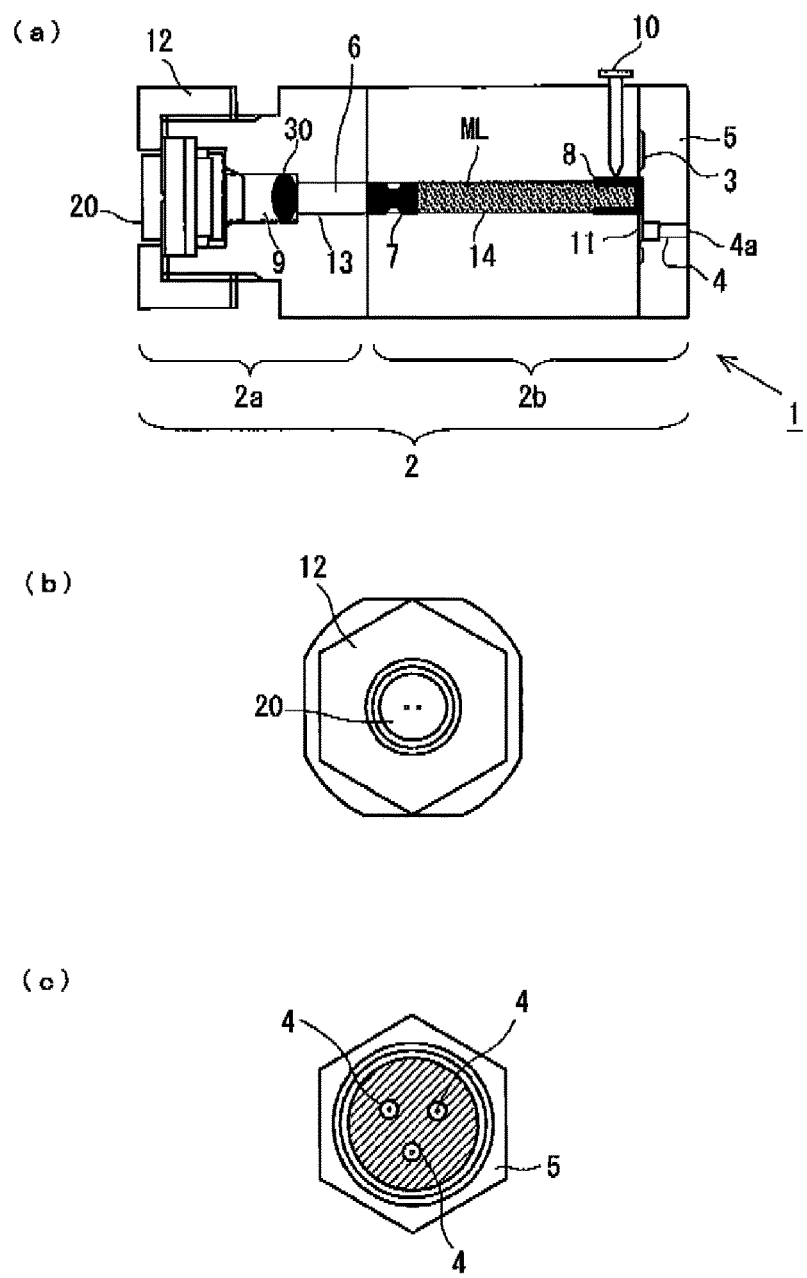
FIG. 1 shows a schematic arrangement of a needleless syringe according to the present invention.

In this embodiment, the main syringe body 2 is roughly classified into a pressurizing unit 2a in which the combustion chamber 9 and the initiator 20 are principally arranged, and an accommodating unit 2b in which the accommodating chamber 14 is principally provided. The state shown in FIG. 1(a) illustrates such a state that the pressurizing unit 2a and the accommodating unit 2b are connected and assembled into one unit. In FIG. 1, any connecting mechanism (for example, screw or the like) for connecting the both units are omitted from the illustration. In the description described later on, a state, in which the pressurizing unit 2a and the accommodating unit 2b are not connected yet, will be referred to on the basis of FIG. 3.

Figure 2:
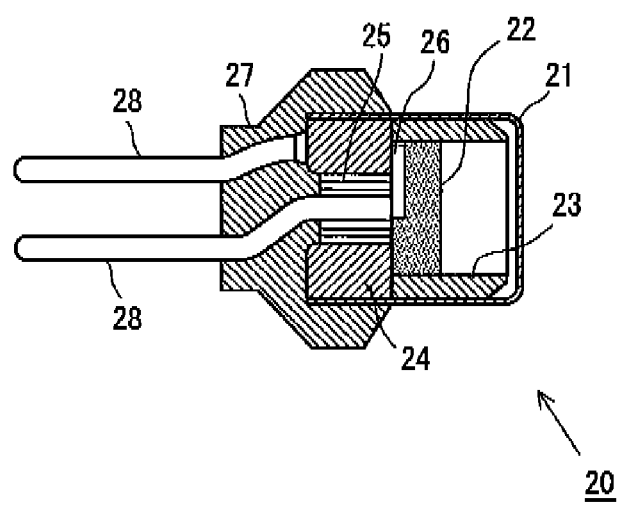
FIG. 2 shows a schematic arrangement of an initiator (ignition device) installed to the needleless syringe shown in FIG. 1.

An example of the initiator 20 will now be explained on the basis of FIG. 2. The initiator 20 is an electric ignition device. A space for arranging an ignition charge 22 is defined in a cup 21 by the cup 21 having a surface covered with an insulating cover. A metal header 24 is arranged in the space, and a cylindrical charge holder 23 is provided on an upper surface thereof. The ignition charge 22 is held by the charge holder 23. A bridge wire 26, which electrically connects one conductive pin 28 and the metal header 24, is wired at the bottom portion of the ignition charge 22. Two conductive pins 28 are fixed to the metal header 24 with an insulator 25 intervening therebetween so that they are in a mutually insulated state. Further, an opening of the cup 21, from which the two conductive pins 28 supported by the insulator 25 extend, is protected by a resin 27 in a state in which the insulation performance is maintained to be satisfactory between the conductive pins 28.

In the initiator 20 constructed as described above, when the voltage is applied between the two conductive pins 28 by an external power source, then the current flows through the bridge wire 26, and the ignition charge 22 is combusted thereby. In this situation, the combustion product, which is produced by the combustion of the ignition charge 22, is spouted from the opening of the charge holder 23. Accordingly, in the present invention, the relative positional relationship of the initiator 20 with respect to the main syringe body 2 is designed so that the combustion product of the ignition charge 22, which is produced in the initiator 20, flows into the combustion chamber 9. Further, an initiator cap 12 is formed to have a brim-shaped cross section so that the initiator cap 12 is hooked by the outer surface of the initiator 20, and the initiator cap 12 is screw-fixed to the main syringe body 2. Accordingly, the initiator 20 is fixed to the main syringe body 2 by means of the initiator cap 12.

Thus, the initiator 20 itself can be prevented from being disengaged from the main syringe body 2, which would be otherwise disengaged by the pressure brought about upon the ignition in the initiator 20.

The ignition charge 22, which is used for the syringe 1, is preferably exemplified by a propellant or explosive (ZPP) containing zirconium and potassium perchlorate, a propellant (THPP) containing titanium hydride and potassium perchlorate, a propellant (TiPP) containing titanium and potassium perchlorate, a propellant (APP) containing aluminum and potassium perchlorate, a propellant (ABO) containing aluminum and bismuth oxide, a propellant (AMO) containing aluminum and molybdenum oxide, a propellant (ACO) containing aluminum and copper oxide, and a propellant (AFO) containing aluminum and iron oxide, or a propellant composed of a combination of a plurality of the foregoing propellants. The propellants or pyrotechnic charge as described above exhibit such a characteristic that the plasma having a high temperature and a high pressure is generated during the combustion immediately after the ignition, but the generated pressure is suddenly lowered because no gas component is contained when the ordinary temperature is given and the combustion product is condensed. It is allowable that any propellant or pyrotechnic charge other than the above is used without any problem, provided that the adequate injection can be performed.

In this embodiment, a gas producing agent 30 having a columnar shape, which is combusted by the combustion product produced by the combustion of the ignition charge 22 to produce the gas, is arranged in the combustion chamber 9. The gas producing agent 30 is exemplified, for example, by a single base smokeless propellant or explosive composed of 98% by mass of nitrocellulose, 0.8% by mass of diphenylamine, and 1.2% by mass of potassium sulfate by way of example. It is also possible to use various gas producing agents used for a gas generator (gas producer) for an airbag and a gas generator (gas producer) for a seal belt pretensioner. Unlike the ignition charge 22 described above, in the case of the gas producing agent 30, the predetermined gas, which is produced during the combustion, contains the gas component even at the ordinary temperature. Therefore, the rate of decrease in the generated pressure is small as compared with the ignition charge 22 described above. Further, the combustion completion time upon the combustion of the gas producing agent 30 is long as compared with the ignition charge 22 described above. However, it is possible to change the combustion completion time of the gas producing agent 30 by adjusting the dimension, the size, and/or the shape, especially the surface shape of the gas producing agent 30 when the gas producing agent 30 is arranged in the combustion chamber 9. This is because the contact state, which is provided with respect to the combustion product of the ignition charge 22 allowed to flow into the combustion chamber 9, is considered to be changed depending on the surface shape of the gas producing agent 30 and the relative positional relationship between the gas producing agent 30 and the ignition charge 22 resulting from the arrangement of the gas producing agent 30 in the combustion chamber 9.

In the next place, the piston 6 made of metal is arranged in the piston chamber 13 so that the piston 6 is slidably movable into the accommodating chamber 14 connected to the piston chamber 13 and the piston 6 is slidable therein in the axial direction. The syringe 1 shown in FIG. 1 is attached so that one end of the piston 6 is exposed on the side of the combustion chamber 9 and the sealing member 7 is brought in contact with the other end. The injection solution ML, which is the injection objective substance to be injected by the syringe 1, is accommodated in the space which is formed in the accommodating chamber 14 between the sealing member 7 and another sealing member 8 arranged at the end portion on the side of the accommodating chamber 14 on which the sealing member 7 is not arranged. Therefore, the accommodating unit of the syringe concerning the present invention is formed by the sealing members 7, 8 and the accommodating chamber 14. The sealing member 7 is made of rubber having the surface thinly coated with silicon oil so that the injection solution does not leak when the injection solution ML is enclosed, and the injection solution ML can be smoothly moved in the accommodating chamber 14 in accordance with the sliding movement of the piston 6. On the other hand, the sealing member 8 is formed to have a thin film-shaped form, and the sealing member 8 is such a member that the thin film can be cleaved and destroyed by means of the force exerted from the outside. The sealing members 7, 8 will be further described later on.

In this arrangement, a holder 5, to which the nozzles 4 for injecting the injection solution ML are installed, is provided on the forward end side of the syringe 1 (right side as shown in FIG. 1). The holder 5 is fixed to the end surface of the main syringe body 2 with a gasket 3 intervening therebetween. In FIG. 1, details of the mechanism (for example, screw or the like) for fixing the holder 5 to the main syringe body 2 are omitted from the illustration.

Further, a flow passage 11 is formed at a portion of the holder 5 brought in contact with the side of the main syringe body 2 so that the injection solution ML released from the accommodating chamber 14 is guided to the nozzle 4. Accordingly, the released injection solution ML passes through the flow passage 11, and the injection solution ML is discharged from the discharge port 4a of the nozzle 4 to the injection target. A plurality of nozzles 4 may be formed in the holder 5. Alternatively, one nozzle 4 may be formed. When the plurality of nozzles are formed, the flow passages, which correspond to the respective nozzles, are formed so that the released injection solution is fed to the respective nozzles. Further, when the plurality of nozzles 4 are formed, as shown in FIG. 1(c), it is preferable that the respective nozzles are arranged at equal intervals around the central axis of the syringe 1. In this embodiment, the three nozzles 4, which are provided for the holder 5, are arranged at equal intervals around the central axis of the syringe 1. The diameter of the nozzle 4 is appropriately set while considering, for example, the injection target, the output pressure (injection pressure) applied to the injection solution ML, and the physical property (viscosity) of the injection solution.

Figure 3:
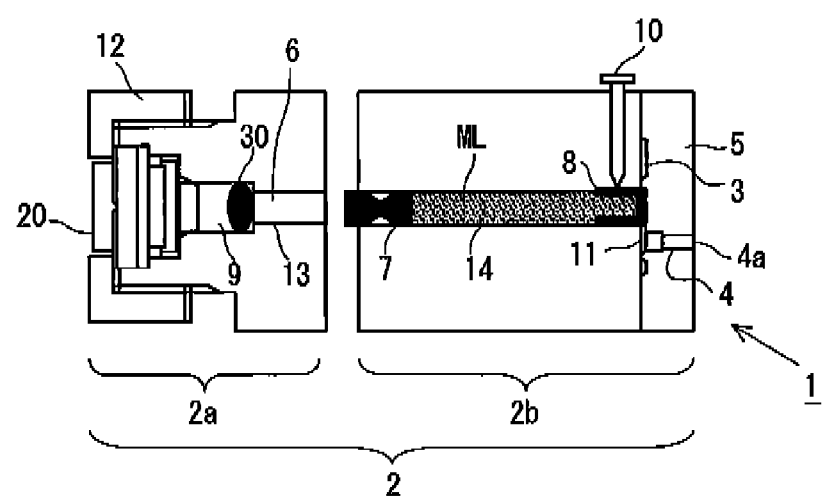
FIG. 3 shows a state provided before an accommodating unit and a pressurizing unit are assembled in relation to the needleless syringe shown in FIG. 1.

An explanation will now be made on the basis of FIG. 3 about the assembling of the pressurizing unit 2a and the accommodating unit 2b. The construction shown in FIG. 3 resides in such a state that the holder 5 has been already assembled to the accommodating unit 2b. In a state provided before the pressurizing unit 2a and the accommodating unit 2b are connected to one another, as shown in FIG. 3, the end portion of the sealing member 7 is in a state of slightly protruding from the end surface of the accommodating unit 2b which is disposed on the side opposed to the pressurizing unit 2a. The sealing member 7 has a cutout formed at the inside thereof. The sealing member 7 has such a shape that when the sealing member 7 receives the external force in the axial direction of the accommodating chamber 14 in a state of being accommodated in the accommodating chamber 14 as shown in FIG. 3, the sealing member can be deformed and contracted in the accommodating chamber 14 by means of the cutout. Therefore, when the pressurizing unit 2a and the accommodating unit 2b are connected, the end portion of the sealing member 7 receives the force from the side of the pressurizing unit 2a. Thus, the sealing member 7 is accommodated in a state of being deformed and contracted in the accommodating chamber 14. As a result, as shown in FIG. 1, in the state in which the pressurizing unit 2a and the accommodating unit 2b are connected, the injection solution ML, which is accommodated in the accommodating chamber 14, is in such a state that a certain or constant force is applied by the sealing member 7. It is noted that the sealing member 8 has a strength of such an extent that the sealing member 8 is not cleaved and destroyed in the pressurized state brought about by the sealing member 7.

In the syringe 1 constructed as described above, the combustion product or the predetermined gas is produced in the combustion chamber 9 by means of the igniter 22 included in the initiator 20 and the gas producing agent 30 arranged in the combustion chamber 9, and the pressure is applied to the injection solution ML accommodated in the accommodating chamber 14 by the aid of the piston 6 and the sealing member 7. As a result, the sealing member 8 is greatly destroyed. The injection solution ML accommodated in the accommodating chamber 14 is extruded to the forward end side of the syringe 1, and the injection solution ML is discharged to the injection target via the flow passage 11 and the nozzle 4. The pressure, which is brought about by the initiator 20 and the gas produced from the gas producing agent 30, is applied to the discharged injection solution ML. Therefore, the injection solution ML penetrates through the surface of the injection target, and the injection solution arrives at the inside thereof. Accordingly, it is possible to achieve the object of injection by using the syringe 1.

In the meantime, the preparatory state for the injection or discharge exists for the syringe 1 according to the present invention between the unused state shown in FIG. 1 (i.e., the state provided before the pressurization is performed by the initiator 20) and the state in which the discharge of the injection solution ML is executed by the pressurization by the initiator 20. The preparatory state is realized by the cleaving means 10, 46, 51 shown, for example, in FIG. 1 as well as FIGS. 4A, 5, 6, and 7 as described later on. Accordingly, embodiments concerning the preparatory state will be explained in detail below.

First Embodiment

Figure 4B:
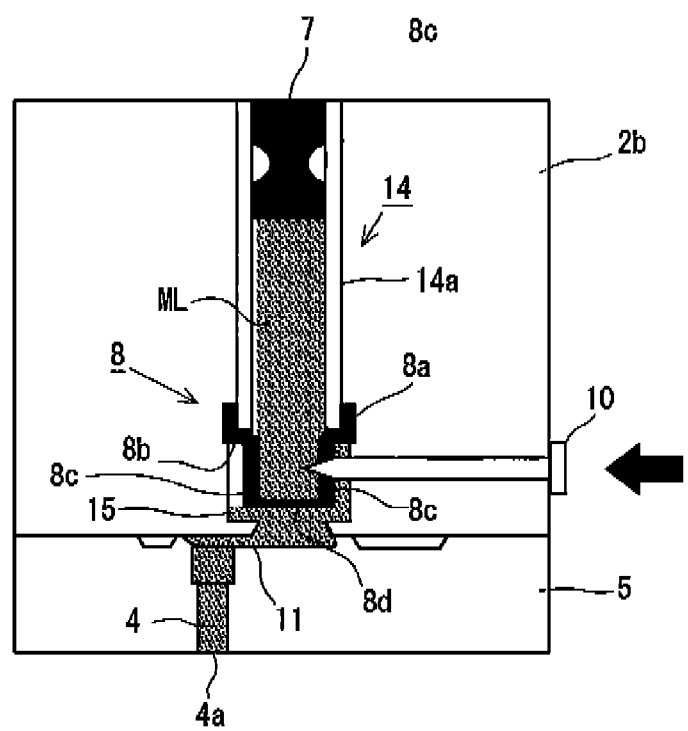
FIG. 4B shows an internal state of the needleless syringe after the interior of the nozzle is preparatorily filled with the injection solution in the first embodiment of the needleless syringe according to the present invention.

FIGS. 4A and 4B show internal situations of the syringe 1 in relation to a first embodiment of the preparatory state for the injection or discharge formed for the syringe 1 according to the present invention. Specifically, FIG. 4A shows the internal situation of the syringe 1 in the state provided before the preparatory state is formed, and FIG. 4B shows the internal situation of the syringe 1 in the state in which the preparatory state has been formed. In the both drawings, the pressurizing unit 2a is omitted from the illustration in order to simplify the drawings. However, as understood from the state of the sealing member 7, FIG. 4A shows the state in which the pressurizing unit 2a is connected to the accommodating unit 2b, and the pressurization, which is exerted on the injection solution ML by the sealing member 7, is continued.

In this embodiment, as shown in FIG. 4A, the accommodating chamber wall 14a for defining the accommodating chamber 14 has a certain or constant thickness. The sealing member 8, which is provided at the end portion of the accommodating chamber 14 on the side of the holder 5, has a cross section having a crank-shaped cap form as shown in FIG. 4A so that a receiving portion 8*b* is provided to receive the thickness of the accommodating chamber wall 14*a*. Specifically, in the cross section of the sealing member 8 shown in FIG. 4A, the sealing member 8 has a wall surface contact portion 8*a* which extends along with the outer surface of the accommodating chamber wall 14*a*, the receiving portion 8*b* which is bent substantially perpendicularly from the wall surface contact portion 8*a* and which receives the thickness of the accommodating chamber wall 14*a* at the end portion of the accommodating chamber 14, and an angular U-shaped (]-shaped) lid portion 8*c* which is connected to the receiving portion 8*b* and which forms a substantial lid at the end portion of the accommodating chamber 14. Owing to the sealing member 8 having the shape as described above, the sealing member 8 is connected to the accommodating chamber wall 14*a* by means of the wall surface contact portion 8*a*, and the injection solution ML is accommodated in the accommodating chamber 14 by means of the lid portion 8*c*. Further, the wall surface contact portion 8*a*, the receiving portion 8*b*, and the lid portion 8*c* are formed to have thin film-shaped forms.

An introducing passage 15, which guides or introduces the injection solution ML accommodated in the accommodating chamber 14 into the flow passage 11 disposed on the side of the holder 5, is formed around the lid portion 8*c* of the sealing member 8. The introducing passage 15 is communicated with the flow passage 11 in the state shown in FIG. 4A. Further, the cleaving means 10 is installed on the side of the lid portion 8*c* of the sealing member 8, i.e., in the direction in which the holder 5 is not connected to the accommodating unit 2*b*. The cleaving means 10 is a pin member having the forward end which has a sharp shape. The proximal end thereof has such a shape that any damage is scarcely caused even when a user of the syringe 1 is brought in contact therewith.

In this arrangement, in the state shown in FIG. 4A, the forward end of the cleaving means 10 is arranged at the position at which the forward end of the cleaving means 10 is not brought in contact with the side surface of the lid portion 8*c* while being opposed thereto. Further, the cleaving means 10 is slidably attached to the accommodating unit 2*b* so that the cleaving means 10 can be pressed in order that the proximal end side thereof can approach the side of the lid portion 8*c* of the sealing member 8 as shown in FIG. 4B. Therefore, starting from the state shown in FIG. 4A, when the cleaving means 10 is pressed and allowed to slide until arrival at the state shown in FIG. 4B, then the forward end of the cleaving means 10 breaks through the thin film disposed on the side of the lid portion 8*c* to destroy a part thereof, and the forward end of the cleaving means 10 arrives at the injection solution accommodated in the accommodating chamber 14.

In this situation, such a state has been provided that the predetermined pressure is applied by the deformed sealing member 7 to the injection solution ML accommodated in the accommodating chamber 14. Therefore, when the thin film of the lid portion 8*c* of the sealing member 8 is broken through, then a part of the injection solution ML flows out to the introducing passage 15 existing around the lid portion 8*c* by using the applied pressure as the driving source, and the part of the injection solution ML arrives at the terminal end of the flow passage at the inside of the nozzle 4, i.e., the discharge port 4*a* via the flow passage 11 communicated with the introducing passage 15. In general, the diameter of the discharge port 4*a* is relatively small, and hence the surface tension, which is generated at the discharge port 4*a*, is large. Therefore, the injection solution, which is allowed to outflow from the lid portion 8*c* of the sealing member 8 by the cleaving means 10, is in such a state that the nozzle 4, the flow passage 11, and the introducing passage 15 are filled therewith, and the outflow of the injection solution from the accommodating chamber 14 approximately stops in this state. It is preferable that the pressure, which is to be applied to the injection solution by the sealing member 7, is adjusted beforehand so that the outflow of the injection solution adequately stops as described above.

In this way, the preparatory state is formed as shown in FIG. 4B in accordance with the sliding movement of the cleaving means 10 in order to discharge the injection solution. In this preparatory state, the flow passage, which ranges to the discharge port 4*a* disposed at the inside of the nozzle 4, is filled with the injection solution before the discharge, i.e., before the pressurization is performed by the initiator 20. Therefore, when the pressurization is performed by the initiator 20, the flow passage, which ranges to the discharge port 4*a*, has been already filled with the injection solution. Therefore, the change of the pressure, which is received by the nozzle 4 from the injection solution upon the injection, can be made gentle or mild as compared with such a state that the flow passage, which ranges to the discharge port 4*a*, is not filled with the injection solution (i.e., such a state that the interior of the nozzle 4, the introducing passage 15, and the flow passage 11 are filled with the atmospheric air). When the pressure change is relieved or alleviated as described above, the load exerted on the nozzle 4 can be mitigated thereby. It is possible to avoid the deformation and the destruction of the nozzle 4, and it is possible to reduce the noise during the discharge.

Further, as shown in FIG. 4B, the cleaving means 10 is in such a state that the cleaving means 10 pierces the side portion of the lid portion 8*c* in the preparatory state. On the other hand, when the pressurization is performed by the initiator 20, the pressure is applied in the axial direction of the accommodating chamber 14, i.e., in the direction directed from the sealing member 7 to the holder 5. In this situation, as clarified from FIG. 4B as well, the forward end of the cleaving means 10 protrudes into the accommodating chamber 14, but the cleaving means 10 itself does not exist at any position at which the advance of the pressure is greatly prohibited. Therefore, the pressure brought about by the initiator 20 is effectively transmitted to the lid portion 8*c* of the sealing member 8, and the lid portion 8*c* is greatly destroyed. Accordingly, the injection solution is allowed to flow into the nozzle 4 via the flow passage 11, and the injection solution is injected or discharged. Further, the lid portion 8*c* is destroyed to a great extent as well. Therefore, for example, destroyed fragments thereof do not prohibit the flow of the injection solution during the discharge. It is also appropriate that the cleaving means 10 returns the state shown in FIG. 4A after cleaving the sealing member 8 by using any elastic means such as a spring or the like for the cleaving means 10.

In the case of the syringe 1 according to this embodiment, the three nozzles 4 are installed for the holder 5 as shown in FIG. 1(*c*). When it is intended to simultaneously discharge the injection solution from the plurality of nozzles as described above, then the interiors of the plurality of nozzles are previously or preparatorily filled with the injection solution as shown in FIG. 4B as described above, and thus it is easy to uniformly or equivalently transport the injection solution to the respective nozzles. This greatly contributes to the realization of the preferred injection (discharge from the respective nozzles without any unevenness), which is also preferred in view of the efficacy.

The syringe 1 constructed as described above makes it possible to realize the preferred injection with respect to the objective injection target by adjusting the pressurization exerted on the injection solution ML by the initiator 20. The injection target of the syringe 1 according to the present invention is the skin structure of the living body such as human, farm animal or the like. The human skin is constructed in a layered form including epidermis, dermis, subcutaneous tissue (hypodermis), and muscular tissue as disposed in the depth direction from the side of the skin surface. Further, the epidermis can be distinguished or classified into horny layer and intradermis in a layered form. In each of the layers of the skin structure, the tissue and the main cells or the like for constructing the tissue have different features as well. In this way, the skin structure of human is generally formed in the layered form. The intrinsic anatomical function is exhibited, for example, by the cells and the tissue principally contained in each of the layers. This means the fact that it is desirable to inject a component (ingredient) for a medical treatment to a place (depth) of the skin structure in conformity with the purpose of the medical treatment, for example, when the medical treatment is applied to the skin. For example, the dendritic cells exist in the intradermis. Therefore, when a vaccine injection is performed therein, it is possible to expect a more effective antigen-antibody reaction.

Further, fibroblasts and collagen cells exist in the dermis. Therefore, for example, if protein for removing skin wrinkles, enzyme, vitamin, amino acid, mineral, sugar, nucleic acid, and various growth factors (epithelial cells and fibroblasts) are injected into the dermis, an effective beauty treatment effect is expected. As for a hair regeneration treatment, the hair roots are positioned in the dermis. Therefore, in order to perform the hair regeneration treatment, the following procedure is considered to be favorable. That is, for example, a stem cell injection method, in which dermal papilla cells and/or epidermal stem cells are autologous cultured and cultured cells are autologous transplanted to the scalp, is performed, or several types of growth factors and/or nutrient components extracted from stem cells (for example, dermal papilla cells, hair root stem cells, epidermal stem cells, HARG cocktail, and hair for transplantation) are injected into a portion positioned in the vicinity of the dermis.

According to the syringe 1 concerning the present invention, for example, cultured cells or stem cells can be seeded or inoculated with respect to cells or scaffold tissue (scaffold) as the injection target in the field of the regenerative medicine, other than the case in which the injection solution is injected into the skin structure as described above. For example, as described in JP2008-206477A, it is possible to inject, by the syringe 1, cells which may be appropriately determined by those skilled in the art depending on the portion subjected to the transplantation and the purpose of the cell regeneration, for example, endothelial cell, endothelial precursor cell, myeloid cell, preosteoblast, chondrocyte, fibroblast, skin cell, muscle cell, liver cell, kidney cell, intestinal tract cell, and stem cell, as well as every cell considered in the field of the regenerative medicine.

Further, the syringe 1 according to the present invention can be also used to deliver DNA or the like, for example, to cells or scaffold tissue (scaffold) as described in JP2007-525192W. In this case, it is possible to suppress the influence exerted, for example, on cells themselves or scaffold tissue (scaffold) itself when the syringe 1 according to the present invention is used, as compared with when the delivery is performed by using any needle. Therefore, it is affirmed that the use of the syringe 1 according to the present invention is more preferred.

Further, the syringe 1 according to the present invention is also preferably used, for example, when various genes, cancer suppressing cells, or lipid envelops are directly delivered to the objective tissue and when the antigen gene is administered in order to enhance the immunity against the pathogen. Other than the above, the syringe 1 can be also used, for example, for the field of the medical treatment for various diseases (field as described, for example, in JP2008-508881W and JP2010-503616W) and the field of the immunological medical treatment (immunotherapy) (field as described, for example, in JP2005-523679W). The field, in which the syringe 1 is usable, is not intentionally limited.

Second Embodiment

Figure 5A:
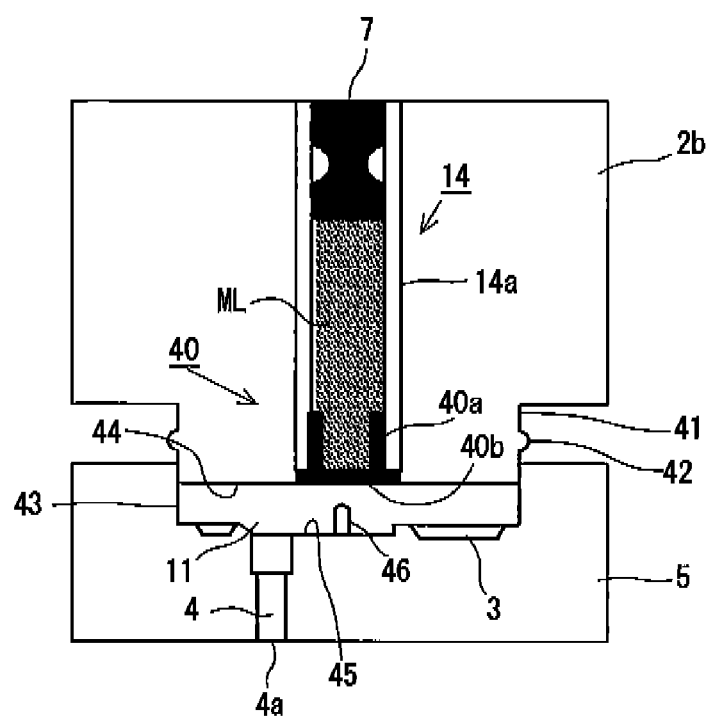
FIG. 5A shows an internal state of the needleless syringe before the interior of the nozzle is preparatorily filled with an injection solution in a second embodiment of the needleless syringe according to the present invention.
Figure 5B:
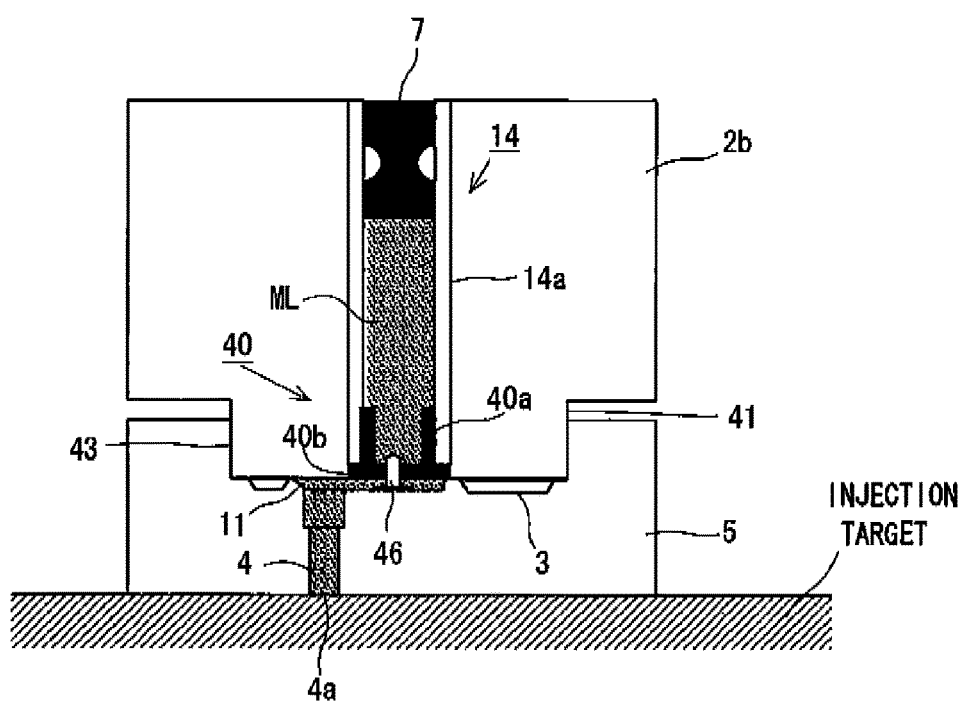
FIG. 5B shows an internal state of the needleless syringe after the interior of the nozzle is preparatorily filled with the injection solution in the second embodiment of the needleless syringe according to the present invention.

FIGS. 5A and 5B show the internal situations of the syringe 1 in relation to a second embodiment of the preparatory state for the discharge as formed for the syringe 1 according to the present invention. Specifically, FIG. 5A shows the internal situation of the syringe 1 in the state provided before the preparatory state is formed, and FIG. 5B shows the internal situation of the syringe 1 in the state in which the preparatory state has been formed. In the both drawings, the pressurizing unit 2a is omitted from the illustration in order to simplify the drawings. However, as understood from the state of the sealing member 7, FIG. 5A shows the state in which the pressurizing unit 2a is connected to the accommodating unit 2b, and the pressurization, which is exerted on the injection solution ML by the sealing member 7, is continued.

In this embodiment, as shown in FIG. 5A, an accommodating chamber wall 14a for defining the accommodating chamber 14 has a certain or constant thickness. A sealing member 40, which is different from the sealing member 8 according to the first embodiment described above, is arranged at the end portion of the accommodating chamber 14 on the side of the holder 5. Specifically, in the cross section of the sealing member 40 shown in FIG. 5A, the sealing member 40 has a wall surface contact portion 40a which extends along with the inner surface of the accommodating chamber wall 14a, and a lid portion 40b which is substantially perpendicular to the wall surface contact portion 40a and which extends in a planar form in the cross-sectional direction of the accommodating chamber wall 14a. Owing to the sealing member 40 having the shape as described above, the sealing member 40 is connected to the accommodating chamber wall 14a by means of the wall surface contact portion 40a, and the injection solution ML is accommodated in the accommodating chamber 14 by means of the lid portion 40b. Further, the wall surface contact portion 40a and the lid portion 40b are formed to have thin film-shaped forms.

In the syringe 1 according to this embodiment, the holder 5 is connected in such a state that the holder 5 is relatively movable with respect to the accommodating unit 2b. Specifically, as shown in FIG. 5A, a columnar neck portion 41 is connected to the end portion of the accommodating unit 2b, and the respective components are arranged so that the flat surface of the lid portion 40b of the sealing member 40 attached to the accommodating chamber 14 described above is substantially flush with the end surface 44 of the neck portion 41. A projection 42 is provided at an intermediate position of the neck portion 41. On the other hand, the holder 5 is provided with a cylindrical recess 43 which is engageable in a slidable state with respect to the neck portion 41 of the accommodating unit 2b. As for the accommodating unit 2b and the holder 5, the holder 5 slides so that the holder 5 closely approaches the accommodating unit 2b, and thus the state changes from the state shown in FIG. 5A to arrive at the state shown in FIG. 5B. When the state changes from the state shown in FIG. 5A to arrive at the state shown in FIG. 5B, it is necessary for the holder 5 to climb over the projection 42 on the neck portion 41. As a result of the climbing over, the holder 5 is restricted from sliding in the opposite direction to return to the state shown in FIG. 5A again.

In the syringe 1 according to this embodiment constructed as described above, the closed space, which is formed by being interposed by the end surface 44 of the neck portion 41 and the bottom surface 45 of the recess 43, is the flow passage 11 for introducing the injection solution into the inside of the nozzle 4. Therefore, the volume of the flow passage 11 is changed in accordance with the relative movement of the holder 5 with respect to the accommodating unit 2. In the state shown in FIG. 5A, the holder 5 is relatively separated from the accommodating unit 2, and hence the flow passage 11 is formed to be wider as compared with the state shown in FIG. 5B.

In this arrangement, the cleaving means 46 is installed on the bottom surface 45 of the recess 43. The cleaving means 46 is a rod-shaped pin member having the forward end which has a sharp shape. The proximal end of the cleaving means 46 is fixed on the bottom surface 45, and the cleaving means 46 extends from the bottom surface 45 toward the surface of the lid portion 40b of the sealing member 40. In this arrangement, in the state shown in FIG. 5A, the forward end of the cleaving means 46 is arranged at the position at which the forward end is not brought in contact with the surface of the lid portion 40b while being opposed thereto. When the holder 5 closely approaches the accommodating unit 2b to arrive at the state shown in FIG. 5B, then the forward end of the cleaving means 46 breaks through the thin film surface of the lid portion 40b, and the forward end destroys a part thereof to arrive at the injection solution disposed at the inside of the accommodating chamber 14.

In this situation, such a state has been provided that the predetermined pressure is applied by the deformed sealing member 7 to the injection solution ML accommodated in the accommodating chamber 14. Therefore, when the thin film of the lid portion 40b of the sealing member 40 is broken through, then a part of the injection solution ML arrives at the terminal end of the flow passage at the inside of the nozzle 4, i.e., the discharge port 4a via the flow passage 11 by using the applied pressure as the driving source. In general, the diameter of the discharge port 4a is relatively small, and hence the surface tension, which is generated at the discharge port 4a, is large. Therefore, the injection solution, which is allowed to outflow from the lid portion 40b of the sealing member 40 by the cleaving means 46, is in such a state that the nozzle 4 and the flow passage 11 are filled therewith, and the outflow of the injection solution from the accommodating chamber 14 approximately stops in this state. It is preferable that the pressure, which is to be applied to the injection solution by the sealing member 7, is adjusted beforehand so that the outflow of the injection solution preferably stops as described above.

In this way, the cleaving means 46 closely approaches the lid portion 40b in accordance with the sliding movement of the holder 5 with respect to the accommodating unit 2b to form the preparatory state for discharging the injection solution as shown in FIG. 5B. The injection solution is discharged in such a state that the discharge port 4a of the nozzle 4 installed in the holder 5 is brought in contact with the injection target. Therefore, the user presses the end surface of the holder 5 of the syringe 1 in the state shown in FIG. 5A against the injection target to apply the load by gripping (for example, any portion of the main syringe body 2). Thus, it is possible to allow the holder 5 to relatively closely approach the accommodating unit 2b to provide the state shown in FIG. 5B. In this state, the discharge port 4a is retained in a state of being brought in contact with the injection target. Therefore, any leakage of the injection solution with which the nozzle 4 or the like is previously or preparatorily filled is scarcely caused. As for the user, the injection solution can be discharged by activating the initiator 20 as it is. Therefore, it is unnecessary to expressly perform the distinguished step in order to form the preparatory state as shown in the first embodiment described above. The convenience for the user is maintained to be higher.

Further, the preparatory state shown in FIG. 5B is formed, and thus the pressure change, which is received by the nozzle 4 from the injection solution during the injection or discharge of the injection solution, can be made gentle or mild as compared with the state in which the flow passage ranging to the discharge port 4a is not filled with the injection solution, in the same manner as in the first embodiment. When the pressure change is relieved or alleviated as described above, then it is possible to mitigate the load exerted on the nozzle 4 thereby, it is possible to avoid the deformation and the destruction thereof, and it is possible to reduce the noise during the discharge. Further, when the plurality of (three in this embodiment) nozzles 4 are previously or preparatorily filled with the injection solution as described above, it is easy to uniformly or equivalently transport the injection solution to the respective nozzles, which is considered to greatly contribute to the realization of the preferred injection (discharge without any unevenness in relation to the respective nozzles) and which is preferred in view of the efficacy as well.

Further, as shown in FIG. 5B, the rod-shaped cleaving means 46 is in the state in which the cleaving means 46 pierces substantially perpendicularly through the surface of the lid portion 40b in the preparatory state. Therefore, the cleaving means 46 does not greatly inhibit the advance of the pressure transmitted through the injection solution when the pressurization is performed by the initiator 20. Therefore, the pressure brought about by the initiator 20 is effectively transmitted to the lid portion 40b of the sealing member 40, and the lid portion 40b of the sealing member 40 is greatly destroyed. Thus, the injection solution is allowed to flow into the nozzle 4 via the flow passage 11, and the injection solution is discharged. Further, the lid portion 40b is greatly destroyed as well. Therefore, for example, destroyed fragments thereof do not prohibit the flow of the injection solution when the injection solution is discharged.

Third Embodiment

Figure 6A:
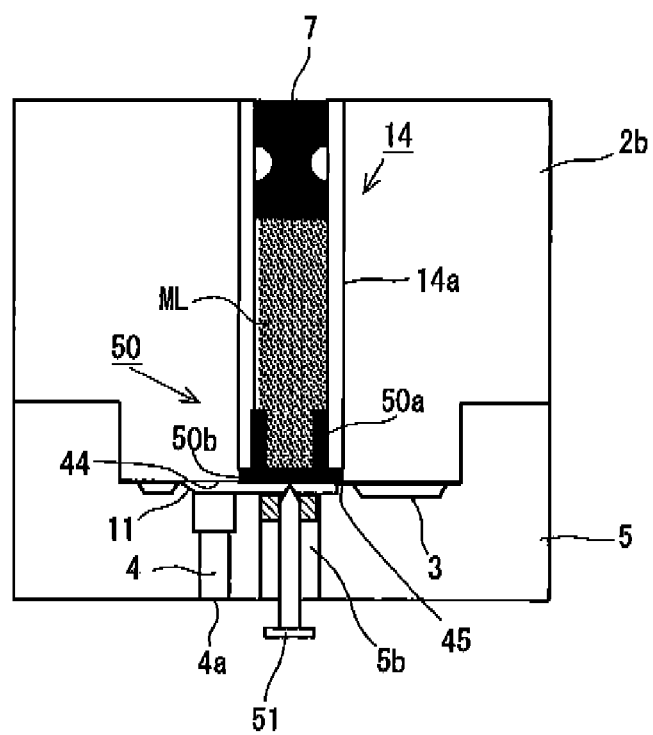
FIG. 6A shows an internal state of the needleless syringe before the interior of the nozzle is preparatorily filled with an injection solution in a third embodiment of the needleless syringe according to the present invention.
Figure 6B:
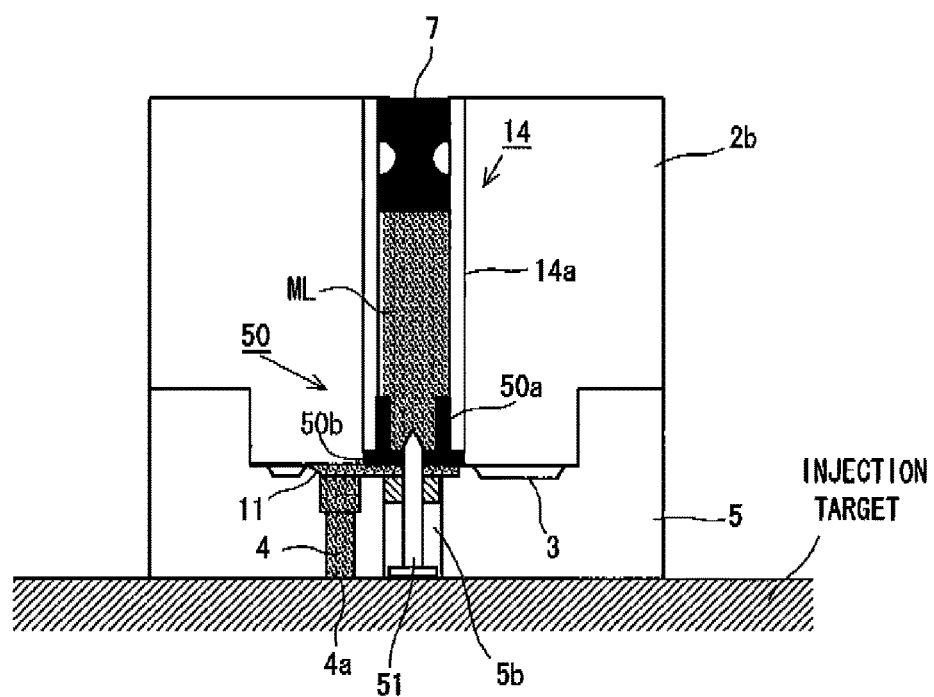
FIG. 6B shows an internal state of the needleless syringe after the interior of the nozzle is preparatorily filled with the injection solution in the third embodiment of the needleless syringe according to the present invention.

FIGS. 6A and 6B show the internal situations of the syringe 1 in relation to a third embodiment of the preparatory state for the discharge as formed for the syringe 1 according to the present invention. Specifically, FIG. 6A shows the internal situation of the syringe 1 in the state provided before the preparatory state is formed, and FIG. 6B shows the internal situation of the syringe 1 in the state in which the preparatory state has been formed. In the both drawings, the pressurizing unit 2a is omitted from the illustration in order to simplify the drawings. However, as understood from the state of the sealing member 7, FIG. 6A shows the state in which the pressurizing unit 2a is connected to the accommodating unit 2b, and the pressurization, which is exerted on the injection solution ML by the sealing member 7, is continued.

In this embodiment, as shown in FIG. 6A, an accommodating chamber wall 14a for defining the accommodating chamber 14 has a certain or constant thickness. A sealing member 50, which is different from the sealing member 8 according to the first embodiment described above, is provided at the end portion of the accommodating chamber 14 on the side of the holder 5. The sealing member 50 is constructed in the same manner as the sealing member 40 according to the second embodiment described above, and the sealing member 50 has a wall surface contact portion 50a which corresponds to the wall surface contact portion 40a and a lid portion 50b which corresponds to the lid portion 40b. On the other hand, the holder 5 according to this embodiment is fixedly connected to the accommodating unit 2b in the same manner as in the first embodiment. A flow passage 11 is formed on a bottom surface 45 disposed on the side of the holder 5, which is adjacent to the lid portion 50b of the sealing member 50, and the flow passage 11 is communicated with the nozzle 4 in this construction.

In this arrangement, a hole 5b, which is open to the outer end surface of the holder 5 (end surface on which the discharge port 4a is open), is provided at a position of the holder 5 opposed to the lid portion 50b of the sealing member 50. The cleaving means 51 is installed, which is supported on the side of the holder 5 in such a state that the cleaving means 51 is slidable in the hole 5b. The cleaving means 51 is a rod-shaped pin member having the forward end which has a sharp shape. The forward end is arranged to extend toward the surface of the bottom portion 50b. The proximal end of the cleaving means 51 has such a shape that any damage is scarcely given to a user even when the user is brought in contact therewith. Any support structure for the cleaving means 51 is omitted from the illustrations of FIGS. 6A and 6B. In both of FIGS. 6A and 6B, such states are shown that the forward end of the cleaving means 51 penetrates through the flow passage 11. However, the portion between the flow passage 11 and the hole 5b is provided with a seal structure so that the injection solution allowed to flow through the flow passage 11 does not flow into the side of the hole 5b.

In the syringe 1 constructed as described above, the forward end of the cleaving means 51 is arranged at the position at which the forward end is not brought in contact with the surface of the lid portion 50b while opposing thereto in the state shown in FIG. 6A. Further, the proximal end of the cleaving means 51 is in such a state that the proximal end protrudes from the outer end surface of the holder 5. Starting from the state shown in FIG. 6A, when the force, which is directed in the upward direction as shown in FIG. 6A, is applied to the protruding proximal end of the cleaving means 51, the cleaving means 51 slides in the hole 5b to arrive at the state shown in FIG. 6B. As a result, the forward end of the cleaving means 51 breaks through the thin film surface of the lid portion 50b, and the forward end destroys a part thereof to arrive at the injection solution accommodated in the accommodating chamber 14.

In this situation, such a state has been provided that the predetermined pressure is applied by the deformed sealing member 7 to the injection solution ML accommodated in the accommodating chamber 14. Therefore, when the thin film of the lid portion 50b of the sealing member 50 is broken through, then a part of the injection solution ML arrives at the terminal end at the inside of the nozzle 4, i.e., the discharge port 4a via the flow passage 11 by using the applied pressure as the driving source. In general, the diameter of the discharge port 4a is relatively small, and hence the surface tension, which is generated at the discharge port 4a, is large. Therefore, the injection solution, which is allowed to outflow from the lid portion 50b of the sealing member 50 by the cleaving means 51, is in such a state that the nozzle 4 and the flow passage 11 are filled therewith, and the outflow of the injection solution from the accommodating chamber 14 approximately stops in this state. It is preferable that the pressure, which is to be applied to the injection solution by the sealing member 7, is adjusted beforehand so that the outflow of the injection solution preferably stops as described above.

In this way, the forward end of the cleaving means 51 closely approaches the lid portion 50b in accordance with the sliding movement of the cleaving means 51 to form the preparatory state for discharging the injection solution as shown in FIG. 6B. The injection solution is discharged in such a state that the discharge port 4a of the nozzle 4 installed to the holder 5 is brought in contact with the injection target. Therefore, the user presses the outer end surface of the holder 5 of the syringe 1 in the state shown in FIG. 6A against the injection target to apply the load by gripping (for example, any portion of the main syringe body 2). Thus, the proximal end of the cleaving means 51 protruding from the end surface of the holder 5 is pushed into the hole 5b, and thus it is possible to provide the state shown in FIG. 6B. In this state, the discharge port 4a is retained in a state of being brought in contact with the injection target. Therefore, any leakage of the injection solution with which the nozzle 4 or the like is previously filled is scarcely caused. As for the user, the injection solution can be discharged by activating the initiator 20 as it is. Therefore, it is unnecessary to expressly perform the distinguished step in order to form the preparatory state as shown in the first embodiment described above. The convenience for the user is maintained to be higher. Further, as shown in FIG. 6B, the proximal end of the cleaving means 51 is substantially flush with the outer surface of the holder 5 including the discharge port 4a to provide the state of being accommodated in the hole 5b. Therefore, the reaction force is hardly received from the cleaving means 51 to the side of the injection target area when the injection is executed, and thus the convenience is maintained.

Further, the preparatory state shown in FIG. 6B is formed, and thus the pressure change, which is received by the nozzle 4 from the injection solution during the injection or discharge of the injection solution, can be made gentle or mild as compared with the state in which the flow passage ranging to the discharge port 4a is not filled with the injection solution, in the same manner as in the first embodiment. When the pressure change is relieved or alleviated as described above, then it is possible to mitigate the load exerted on the nozzle 4 thereby, it is possible to avoid the deformation and the destruction thereof, and it is possible to reduce the noise during the discharge. Further, when the plurality of (three in this embodiment) nozzles 4 are previously or preparatorily filled with the injection solution as described above, it is easy to uniformly or equivalently transport the injection solution to the respective nozzles, which is considered to greatly contribute to the realization of the preferred injection (discharge without any unevenness in relation to the respective nozzles) and which is preferred in view of the efficacy as well.

Further, as shown in FIG. 6B, the rod-shaped cleaving means 51 is in the state in which the cleaving means 51 pierces substantially perpendicularly through the surface of the lid portion 50b in the preparatory state. Therefore, the cleaving means 51 does not greatly inhibit the advance of the pressure transmitted through the injection solution when the pressurization is performed by the initiator 20. Therefore, the pressure brought about by the initiator 20 is effectively transmitted to the lid portion 50b of the sealing member 50, and the lid portion 50b of the sealing member 50 is greatly destroyed. Thus, the injection solution is allowed to flow into the nozzle 4 via the flow passage 11, and the injection solution is discharged. Further, the lid portion 50b is greatly destroyed as well. Therefore, for example, destroyed fragments thereof do not prohibit the flow of the injection solution when the injection solution is discharged.

Fourth Embodiment

Figure 7A:
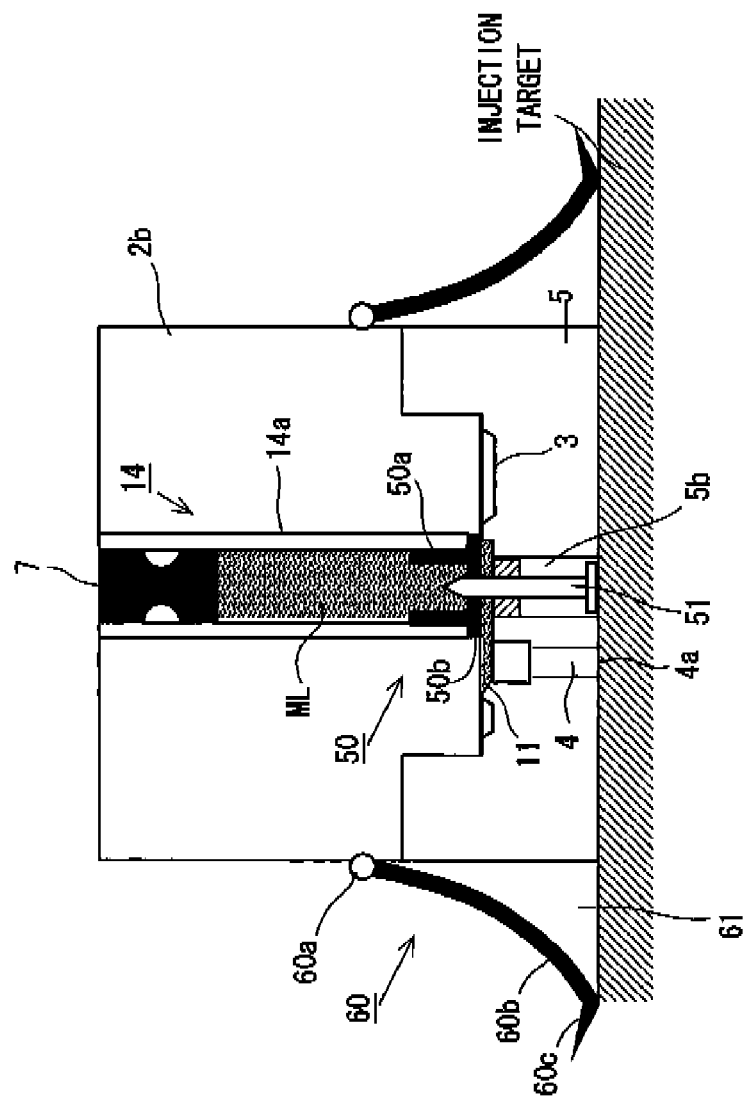
FIG. 7A shows an internal state of the needleless syringe before the interior of the nozzle is preparatorily filled with an injection solution in a fourth embodiment of the needleless syringe according to the present invention.
Figure 7B:
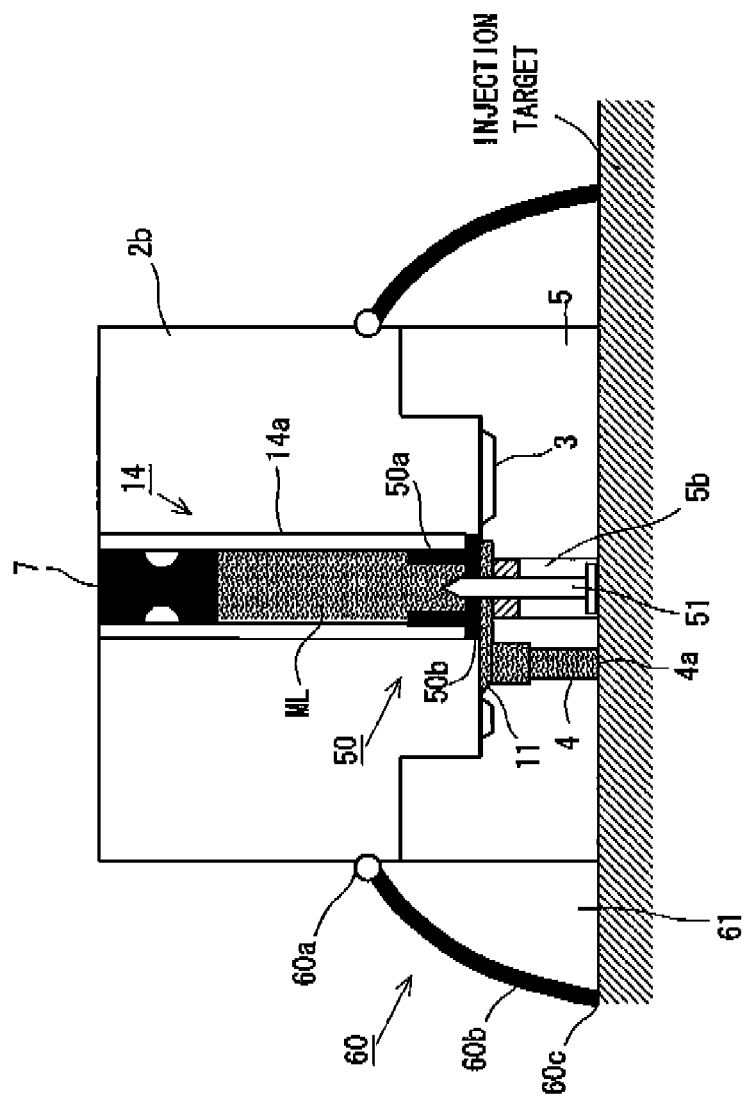
FIG. 7B shows an internal state of the needleless syringe after the interior of the nozzle is preparatorily filled with the injection solution in the fourth embodiment of the needleless syringe according to the present invention.

FIGS. 7A and 7B show the internal situations of the syringe 1 in relation to a fourth embodiment of the preparatory state for the discharge as formed for the syringe 1 according to the present invention. Specifically, FIG. 7A shows the internal situation of the syringe 1 in the state provided before the preparatory state is formed, and FIG. 7B shows the internal situation of the syringe 1 in the state in which the preparatory state has been formed. This embodiment has the common construction as compared with the third embodiment described above except that a shutoff wall 60 is provided on the side surface of the accommodating unit 2b. Therefore, the constitutive components or parts other than those relevant to the shutoff wall 60 are designated by the same reference numerals as those of FIGS. 6A and 6B, any detailed explanation of which will be omitted.

The shutoff wall 60, which is composed of a rubber piece 60b, is attached to the side surface of the accommodating unit 2b by the aid of the support point 60a. As shown in FIGS. 7A and 7B, the free end 60c of the rubber piece 60b has a size and elasticity which are sufficient to such an extent that the free end 60c can be also brought in contact with the injection target when the discharge port 4a of the syringe 1 is brought in contact with the injection target, and the rubber piece can make the transition between different curved states as shown in FIGS. 7A and 7B ranging from the free end 60c to the support point 60a.

In particular, in the state shown in FIG. 7A, when the discharge port 4a is brought in contact with the injection target, then the cleaving means 51 slides into the hole 5b, and a part of the thin film of the lid portion 50b is cleaved and destroyed. However, such a situation is assumed that the viscosity of the injection solution is relatively high, and/or the diameter of the flow passage 11 and/or the flow passage diameter in the nozzle 4 is/are relatively small, and hence the injection solution, which leaks out from the accommodating chamber 14, does not sufficiently arrive at the opening 4a. In this situation, the free end 60c of the rubber piece 60b is also brought in contact with the injection target, and the rubber piece 60b is in a state of being curved toward the lower side (side near to the injection target as compared with the line for connecting the support point 60a and the free end 60c). This curved state is formed by pressing the rubber piece 60 by the user. In this situation, the closed space 61, which has a certain gas-tight state, is formed around the discharge port 4a of the syringe 1 by the injection target and the shutoff wall 60 including the rubber piece 60b. It is unnecessary that the gas-tight state provided in the closed space 61 is not so strict as the gas-tight state provided when the injection solution is accommodated in the accommodating chamber 14.

Starting from the state shown in FIG. 7A, when the user releases the hand by which the rubber piece 60b has been held or pressed (a slight gap is maintained between the lower end of the holder 5 and the injection target, or a groove to communicate the closed space 61 and the opening 4a is formed at the lower end of the holder 5), the rubber piece 60b returns to the state in which the rubber piece 60b is curved toward the upper side (side opposite to the injection target as compared with the line for connecting the support point 60a and the free end 60c) in accordance with the restoring force of the rubber piece 60b, while the free end 60c is still brought in contact with the injection target. As a result, the volume of the closed space 61 is increased as compared with the volume provided in the state shown in FIG. 7A. Therefore, the pressure state in the closed space 61 is in the negative pressure state. As a result, the portion, which is disposed in the vicinity of the discharge port 4a brought in contact with the injection target, is also in a state approximate to the negative pressure state. The injection solution is sucked and attracted toward the opening 4a in accordance with the pressure difference between the opening 4a and the portion of the flow passage 11 at which the injection solution has arrived. Thus, as shown in FIG. 7B, the state is formed, in which the nozzle 4 and the flow passage 11 are filled with the injection solution.

The shutoff wall 60, which has the rubber piece 60b as described above, is the constitutive component which greatly contributes to the reliable formation of the preparatory state for previously or preparatorily filling the nozzle 4 and the flow passage 11 with the injection solution. Further, when the pressurization is executed by the initiator 20 and/or when the preparatory state is formed, then it is also possible to prohibit the scattering of the injection solution to the circumference or periphery of the discharge port 4a by means of the shutoff wall 60.

PARTS LIST

1: syringe, 2: main syringe body, 2a: pressurizing unit, 2b: accommodating unit, 4: nozzle, 5: holder, 6: piston, 7: sealing member, 8: sealing member, 8c: lid portion, 9: combustion chamber, 10, 41, 51: cleaving means, 11: flow passage, 14: accommodating chamber, 14a: accommodating chamber wall, 15: introducing passage, 20: initiator, 22: igniter, 30: gas producing agent, 40: sealing member, 40b: lid portion, 46: cleaving means, 50: sealing member, 50b: lid portion, 51: cleaving means, 60: shutoff wall, 60b: rubber piece, 61: closed space.

What is claimed is:

1. A needleless syringe for injecting an injection objective substance into an injection target area, the needleless syringe comprising:
  a main syringe body containing the injection objective substance with the use of a sealing member;
  a pressurizing unit provided in the main syringe body and configured to pressurize the injection objective substance;
  a flow passage unit defining a flow passage of the pressurized injection objective substance to be discharged to the injection target area; and
  a preparatory filling unit configured to fill the flow passage unit with a part of the injection objective substance by destroying a part of the sealing member before the injection objective substance is pressurized.

2. The needleless syringe according to claim 1, further comprising an accommodating unit provided in the main syringe body and configured to accommodate the injection objective substance with the aid of the sealing member that contacts the accommodating unit,
wherein:
the sealing member is provided on one end side of an accommodating chamber provided in the main syringe body and a second sealing member is provided on an opposing end side of the accommodating chamber so that the accommodating chamber is hermetically closed; and
the flow passage unit is filled with the part of the injection objective substance by a load exerted on the injection objective substance by the second sealing member when the part of the sealing member is destroyed by the preparatory filling unit.

3. The needleless syringe according to claim 2, wherein the second sealing member is configured to provide a driving force to introduce or guide the injection objective substance accommodated in the accommodating chamber into the flow passage unit when the part of the sealing member disposed on one end side is destroyed by the preparatory filling unit.

4. The needleless syringe according to claim 1, further comprising an accommodating unit provided in the main syringe body and configured to accommodate the injection objective substance with the aid of the sealing member that contacts the accommodating unit,
wherein:
the pressurizing unit is configured to destroy or move the sealing member in an axial direction based on a pressure applied to the injection objective substance in the axial direction of the main syringe body;
the preparatory filling unit has a movable destroying member which is movable toward the sealing member to destroy the part of the sealing member before the injection objective substance is pressurized; and
the movable destroying member is in a non-contact state with respect to the sealing member when the movable destroying member is disposed at a first position, while the movable destroying member is brought in contact with the sealing member to destroy the part of the sealing member when the movable destroying member is moved from the first position to a second position.

5. The needleless syringe according to claim 4, wherein:
the movable destroying member is provided on a side of the flow passage unit, and a part of the movable destroying member is configured to protrude from an outer surface of the flow passage unit on which a discharge port of the flow passage unit is disposed when the movable destroying member is disposed at the first position; and
the movable destroying member, which has protruded, is moved to the second position to destroy the part of the sealing member when the movable destroying member is pressed in a state in which the discharge port is brought in contact with the injection target area.

6. The needleless syringe according to claim 5, wherein an end portion of the movable destroying member disposed at the second position is in a substantially flush state with respect to an outer surface of the flow passage unit for which the discharge port is formed.

7. The needleless syringe according to claim 1, wherein:
the flow passage unit is movably attached to the main syringe body to closely approach the main syringe body before the injection objective substance is pressurized;
the preparatory filling unit is provided on a side of the flow passage unit; and
when the flow passage unit closely approaches the main syringe body before the injection objective substance is pressurized, the part of the sealing member is destroyed by the preparatory filling unit, the flow passage unit is filled with the part of the injection objective substance, and thus the pressurizing unit is ready to pressurize the injection objective substance.

8. The needleless syringe according to claim 7, wherein the flow passage unit relatively closely approaches the main syringe body by being pressed from a side of the main syringe body in a state in which the discharge port is brought in contact with the injection target area.

9. The needleless syringe according to claim 1, wherein the sealing member is formed to have a thin film-shaped form, the preparatory filling unit cleaves the thin film, and thus the flow passage unit is filled with the part of the injection objective substance.

10. The needleless syringe according to claim 1, wherein the preparatory filling unit has a shutoff wall which forms a substantially gas-tight closed space including a discharge port of the flow passage unit and the injection target area in a state in which the discharge port is brought in contact with the injection target area, and wherein an interior of the closed space brought about by the shutoff wall is made in a negative pressure state in a state in which the part of the sealing member is destroyed, and thus the flow passage unit is filled with the part of the injection objective substance.

11. The needleless syringe according to claim 10, wherein the shutoff wall includes an elastic member, and the negative pressure state is formed in the closed space in accordance with elastic deformation of the elastic member.

12. A needleless syringe for injecting an injection objective substance into an injection target area without using any injection needle, the needleless syringe comprising:
a main syringe body;
an accommodating unit which accommodates the injection objective substance by the aid of a sealing member in an accommodating chamber provided in the main syringe body;
a pressurizing unit which pressurizes the injection objective substance accommodated in the accommodating unit to move or destroy the sealing member thereby so that the injection objective substance is discharged to outside;
a flow passage unit which forms a discharge port with respect to the injection target area and which defines a flow passage so that the injection objective substance pressurized by the pressurizing unit is discharged via the discharge port to the injection target area; and
a shutoff wall which forms a substantially gas-tight closed space including the discharge port and the injection target area in a state in which the discharge port is brought in contact with the injection target area.

13. The needleless syringe according to claim 12, wherein an interior of the closed space brought about by the shutoff wall is made in a negative pressure state in a state in which the part of the sealing member is destroyed, and thus the flow passage unit is filled with the part of the injection objective substance.

14. A needleless syringe for injecting an injection objective substance into an injection target area, the needleless syringe comprising:

a pressurizing unit configured to pressurize the injection objective substance;

a discharge port defining a flow passage of the pressurized injection objective substance to be discharged to the injection target area; and a shutoff wall which forms a substantially gas-tight closed space including the discharge port and the injection target area in a state in which the discharge port is brought in contact with the injection target area.

15. The needleless syringe according to claim 14, further comprising an accommodating unit configured to accommodate the injection objective substance with the aid of a sealing member that contacts the accommodating unit, wherein the shutoff wall is configured to at least partially fill the discharge port with the injection objective substance by destroying a part of the sealing member before the injection objective substance is pressurized.

* * * * *